(12) United States Patent
Shah et al.

(10) Patent No.: US 6,460,541 B1
(45) Date of Patent: Oct. 8, 2002

(54) HEAT-SEALED INFLATABLE ARTICLE, AND METHOD OF MAKING THE SAME

(75) Inventors: Tilak M. Shah, Cary, NC (US); Dezso K. Levius, Cary, NC (US)

(73) Assignee: Polyzen, Inc., Cary, NC (US)

( * ) Notice: Subject to any disclaimer, the term of this patent is extended or adjusted under 35 U.S.C. 154(b) by 37 days.

(21) Appl. No.: 09/707,531

(22) Filed: Nov. 7, 2000

(51) Int. Cl.⁷ .............................................. A61G 15/00
(52) U.S. Cl. ...................... 128/845; 128/842; 128/844; 128/918
(58) Field of Search .................. 128/842, 844, 128/918, 845; 604/347–353

(56) References Cited

U.S. PATENT DOCUMENTS

| | | | | |
|---|---|---|---|---|
| 5,331,974 A | * | 7/1994 | Sook | 128/844 |
| 5,469,863 A | * | 11/1995 | Shah | 128/844 |
| 5,679,423 A | * | 10/1997 | Shah | 428/35.2 |
| 5,833,915 A | * | 11/1998 | Shah | 264/491 |
| 5,885,205 A | * | 3/1999 | Kassman | 600/38 |

FOREIGN PATENT DOCUMENTS

WO  WO9814147  * 4/1998

* cited by examiner

Primary Examiner—Michael A. Brown
(74) Attorney, Agent, or Firm—Yongzhi Yang; Steven J. Hultquist; Marianne Fuierer

(57) ABSTRACT

An inflatable structure comprising an inflation compartment defining an enclosed interior volume and an anti-reflux valve having an outlet end positioned in the interior volume. The anti-reflux valve includes an elongate inflation passage including opposedly facing film layers that are bonded to one another at their edges to form an interior gas flow channel. The elongate inflation passage is bonded to the inflatable compartment to form an opening for introduction of gas into the passage, for inflation of the inflation compartment, and arranged so that upon termination of gas flow into the interior volume, after pressure in the interior volume has been raised above exterior pressure on the inflatable compartment, gas pressure in the interior volume collapses the opposedly facing film layers against one another to form a seal against the interior volume gas pressure and maintain the inflation compartment in an inflated state.

19 Claims, 4 Drawing Sheets

HEAT-SEALED INFLATABLE ARTICLE, AND METHOD OF MAKING THE SAME

BACKGROUND OF THE INVENTION

1. Field Of The Invention

The present invention relates to heat-sealed inflatable articles, and to a method of making such articles.

2. Description of the Related Art

In a wide variety of applications, there is a need for a structural article that is readily inflated and deflated, and that in the deflated state can be easily compacted or reposed in a lay-flat state.

Examples include cushions, brace/support structures, pillows, mattresses, flotation devices, packing elements that are inflated to prevent impact/damage to objects being shipped or transported, and the like.

One problem experience in the use of such inflatable articles is that the means for inflation and deflation of such articles are bulky and difficult to use, with a conformation that interferes with the desired lay-flat character of the article.

It therefore is an objective of the present invention to provide an inflatable article that includes inflation/deflation means that in a deflated or unfilled state assume a lay-flat conformation, and that are simply and economically fabricated and readily used to inflate an associated inflatable volume of the article.

It is another object of the invention to provide a method of simply and economically fabricating such a structure.

Other objects and advantages of the invention will be more fully apparent from the ensuing disclosure and appended claims.

SUMMARY OF THE INVENTION

The present invention relates to an inflatable article comprising an inflatable compartment having an anti-reflux valve associated therewith.

In one specific embodiment, the invention relates to an inflatable structure comprising an inflation compartment defining an enclosed interior volume and an anti-reflux valve having an outlet end positioned in the interior volume. The anti-reflux valve comprises an elongate inflation passage including oppositely facing film layers that are bonded to one another at their edges to form an interior gas flow channel, such elongate inflation passage being bonded to the inflatable compartment to form an opening for introduction of gas into the passage, and arranged so that introduced gas flows through the interior gas flow channel, for discharge from the passage into the interior volume of the inflation compartment. The elongate passage extends into the interior volume of the inflatable compartment to a sufficient extent so that upon termination of gas flow into the interior volume, after pressure in the interior volume has been raised above exterior pressure on the inflatable compartment, gas pressure in the interior volume will collapse the oppositely facing film layers against one another to form a seal against the interior volume gas pressure and maintain the inflation compartment in an inflated state.

In a particular embodiment, the inflatable structure is a constituent part of a condom article, and the inflatable compartment is arranged to exert compressive force on the penis, e.g., at the base thereof and/or along the shaft thereof, to enhance an erection of a wearer.

The anti-reflux valve, being formed of film layers, as more fully discussed hereinafter, accommodates the compaction of the inflatable article, and its storage, packaging and support in a lay-flat or other compacted state. In application to a condom, the valve has a thin and pliable character that permits ease of packaging, application and removal of the condom, as well as being unobtrusive in use.

Other aspects, features and embodiments of the invention will be more fully apparent from the ensuing disclosure and appended claims.

DETAILED DESCRIPTION OF THE INVENTION, AND PREFERRED EMBODIMENTS THEREOF

Figure 1:
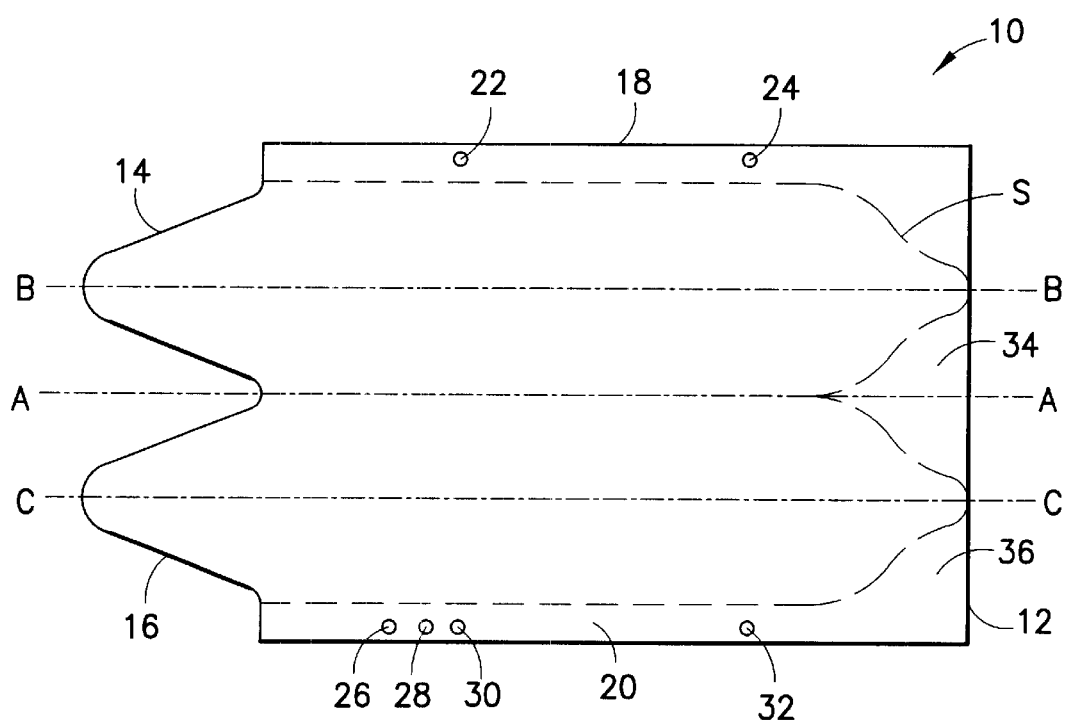
FIG. 1 is a top plan view of a polymeric film blank for forming an inflatable condom article.

The inflatable structure of the present invention comprises a laminate, i.e., a multilayer arrangement of film layers, that include an inflation compartment defining an enclosed interior volume and an anti-reflux valve positioned in the interior volume at its outlet end. The anti-reflux valve is formed by an elongate inflation passage including oppositely facing film layers that are bonded to one another at their edges to form an interior gas flow channel bounded by the film layers. The elongate inflation passage is bonded to the inflatable compartment to form an opening for introduction of gas into the passage. The elongate passage is arranged so that the introduced gas flows through the interior gas flow channel, for discharge at the outlet end of the passage into the interior volume of the inflatable compartment. The elongate passage extends into the interior volume of the inflatable compartment to a sufficient extent so that upon termination of gas flow into the interior volume, after pressure in the interior volume has been raised above exterior pressure on the inflatable compartment, such interior volume pressure will operate to collapse the oppositely facing film layers against one another to form a seal against the interior volume pressure to maintain the inflation compartment in an inflated state.

In a preferred conformation, the oppositely facing film layers of the elongate inflation passage at their outer edges are heat sealed to the layers forming the inflation compartment, as a unitary structure.

Once inflated, as for example by a gas fill tube introduced into the elongate inflation passage and feeding compressed gas into the inflation compartment, the gas fill tube is removed after the pressure in the inflation compartment is above the exterior pressure on the compartment, i.e., on the exterior surface of the compartment. For an inflation compartment in an ambient environment, the exterior pressure is the atmospheric pressure. When the inflation compartment is elevated in its interior pressure, above the exterior pressure, the cessation of gas introduction, such as by removing the gas fill tube, will cause the higher interior pressure in the compartment to "close down" the layers of the elongate inflation passage against one another, sealing the compartment.

Thereafter, the higher interior pressure in the compartment maintains the seal of the anti-reflux valve. If it then is desired to deflate the compartment, the simple insertion of a tube or other implement serving to part the contiguous pressure-sealed layers of the elongate inflation passage will break the seal of the valve and allow the egress of the gas from the interior volume of the inflation compartment to the ambient environment. The gas can be squeezed out of the inflation compartment in this manner, and the deflated article can then be rolled or otherwise compacted, for storage, transport, disposal, etc.

It will therefore be appreciated that prior or subsequent to inflation, the inflatable article can stored or transported in a compacted state, and that the anti-reflux valve, being formed of film layers, is correspondingly flattenable or compactable without contributing significant volume or bulk to the overall article.

The inflatable article of the invention therefore can be readily formed by heat-sealing or other joining techniques commonly known and used in the art for forming structural articles from film materials in the form of web or sheet stock. For example, the laminae of the inflatable article of the present invention can be joined by a suitable welding technique such as RF welding, heat impulse welding, solvent welding, adhesive bonding, etc., with RF welding generally being most preferred. It is also possible to join the respective layers of the structure by adhesive bonding or any other suitable joining means and methods. Preferably, heat impulse welding or RF welding is employed.

The inflation compartment of the inflatable article may have any suitable volume appropriate to its use. Further, it will be appreciated that the inflatable article of the present invention may be of a multi-compartmented nature, with separate or unitary inflation passages for the multiple compartments.

In one embodiment, the inflatable compartment may have an interior inflated volume in a range of from about 0.05 liter to about 5 liters. It will be recognized that the inflated volume of the compartment will depend on the pressure to which the compartment is inflated, and the extensibility or expandable character of the compartment. In the case of elastomeric or elastic materials of construction, the volumetric expansion of the inflation compartment may be significant.

One preferred application of the inflatable structure of the present invention is the provision of inflatable compartment(s) in a condom article, in which the compartment(s) is/are filled with a gas to provide the inflated condom with pressure-exerting capability against the wearer's penis, to enhance and maintain the wearer's erection and to prolong intercourse, by providing a stiffened sheath on the penis. For example, an inflatable compartment may be provided on the condom in the vicinity of its proximal end, so as to provide in the inflated state an exertion of pressure by the condom at the base of the wearer's penis, to maintain an erect penis of the wearer in an engorged condition.

The condom article may be configured as a male condom or a female condom.

For such condom applications, the inflatable compartment and the anti-reflux valve preferably are formed of a film material having a low modulus and a rubbery "hand" character. The modulus (here meaning the modulus of elasticity at 50% elongation), is suitably below about 1500 pounds per square inch (psi), preferably being in the range of from about 50 to about 800 psi, and most preferably in the range of from about 50 to about 500 psi.

The durometer value of the film material for such condom article is suitably below 98 A, being advantageously in the range of from about 90 to about 10 A, more preferably in the range of from about 20 to about 85 A, and most preferably from about 30 A to about 75 A.

Among polymeric film materials useful in the broad practice of the present invention to form the inflatable compartment and the anti-reflux valve, illustrative materials include: polyurethane; styrene-isoprene-styrene/styrene-butadiene-styrene compositions, such as Kraton® polymers (commercially available from Shell Chemical Company, Houston, Tex.); polyvinylchloride (PVC) that has been plasticized to the desired flexibility and hand characteristics; urethane/PVC blends; urethane that has been plasticized to the desired flexibility and hand characteristics; Covale™ polymer (commercially available from Dow Chemical Company, Midland, Mich.); polyester elastomers such as Hytrelt (commercially available from E.I. DuPont de Nemours & Company, Wilmington, Del.); polyamide elastomers such as Pebax® (commercially available from Atochem); olefinic polymers (polypropylene, polyethylene, etc.); and metallocene polymers.

A preferred film material is polyurethane film having a durometer not exceeding about 90 A.

The film material used to fabricate the inflatable article may be used in the form of a blown film, extruded sheet, solvent cast film or other suitable web stock formed of the polymeric material. In addition to the aforementioned polymeric materials, the inflatable articles of the invention may be formed of any other suitable materials, natural or synthetic, that in native form or as treated by suitable treatment methods, possess a sufficiently low gas permeability to be useful for their intended purpose, as regards the maintenance of the inflated condition for the desired duration.

The thickness of the film material used to form the inflatable article of the invention, in a preferred aspect, is typically in the range of from about 1 to about 25 mils, more preferably in the range of from about 2 to about 10 mils, and most preferably in the range of from about 2 to about 6 mils.

The film from which the inflatable article is fabricated can contain dye or pigment additives to impart a desired color to the product structure, and the resins from which the films are formed may be blended with other additives, such as tackifiers, antioxidants, uv stabilizers, dispersing agents, fillers, surfactants, surface modifiers, heat stabilizers, flame retardants, etc., as necessary or desirable to the end use of the inflatable article. The sheet stock used to fabricate the inflatable article can also contain conductive material, e.g., carbon black or metallic particulate materials, to impart conductivity characteristics to the article, if desired in a specific end use application of the invention.

In one illustrative technique for forming the anti-reflux valve and inflatable compartment, radio frequency welding is employed to heat-seal the seam of the inflatable article formed by superposed sheets of polymeric film.

By way of example, for a preferred polyurethane film having a 70A durometer hardness, radio frequency (RF) welding of the edge seams of the superposed sheets can be carried out at a temperature of from about 100° F. to about 300° F., most preferably at a temperature in the vicinity of 250° F. The corresponding RF power level is in the range of from about 100 to about 500 milliamps, most preferably in the vicinity of 400 milliamps. A cycle time for the RF welding operation may be of corresponding duration as necessary to achieve continuous seam welding of the superposed sheets at the seam regions of the sheets.

In one embodiment, a cycle time of 15 seconds of RF welding comprises the following cycle steps:

Preheating 1.5 seconds
RF welding 2.5 seconds
Cooling 1.0 second
Open/close 10 seconds As another variant sheet joining technique, seam joining of the sheets can also be carried out by impulse heating of the superposed polymeric film sheets, at a temperature of from about 300° F. to about 500° F. for a time of from about 3 to about 10 seconds.

As a still further sheet joining technique, adhesive or solvent bonding of the superposed sheets can be carried out, using suitable adhesive formulation or solvent medium. By way of example, solvent bonding of the preferred material polyurethane sheets can be carried out by solvent bonding using tetrahydrofuran (THF) as the solvent bonding medium, or such polyurethane sheets can be adhesively bonded by a THF/polyurethane blend adhesive composition.

The seams themselves must be continuous along their length, to provide the requisite leak-tightness to the product article in the inflated condition. Preferred seam characteristics for polyurethane materials of the above-described types, include a seam dimension that is in the range of from about 0.020 to 0.125 inch, most preferably in the range of from about 0.050 to about 0.050 inch.

In preferred practice, the seam strength of the inflatable compartment should be at least about 1000 pounds per square inch (psi), or altenatively at least about 30% of the strength of the unwelded film.

For impulse heat welding as the welding method used to join the superposed sheets of polymeric film material, the seam dimension is suitably at least twice the thickness of the film stock used in the bag, and preferably the seam dimension does not exceed about 0.5 inch.

Referring now to the drawings, FIG. 1 is a top plan view of a polymeric film blank 10 for forming an inflatable condom article. The polymeric film blank comprises a main sheet 12 having a generally rectangular shape with rearwardly-extending proximal gripping flanges 14 and 16.

The polymeric film sheet 12 may be formed of any suitable material, e.g., polyurethane; styreneisoprene-styrene/styrene-butadiene-styrene compositions; plasticized polyvinyl-chloride; urethane/PVC blends; polyester elastomers; polyamide elastomers; olefinic polymers; metallocene polymers; etc. A preferred material comprises polyurethane film having a durometer not exceeding about 90 A.

The polymeric film material may be formed in any suitable manner. For example, such film material may comprise blown film; extruded sheet; solvent cast film; etc., having any suitable thickness, e.g., a thickness in the range of from about 1 to about 25 mils, more preferably in the range of from about 1 to about 10 mils, and most preferably in the range of from about 2 to about 6 mils.

The polymeric film sheet 12 has a center fold line indicated by dashed line A—A, with respective side margins 18 and 20. The side margin 18 has registration holes 22 and 24 therein, and side margin 20 has registration holes 26, 28, 30 and 32 therein, the functions of which will be more fully apparent from the ensuing description.

It will be appreciated that the centerline A—A divides the polymeric film sheet 12 into two half-sections 34 and 36 that are superposable on one another when the sheet is folded at the centerline A—A, so that margins 18 and 20 are registered with one another. In such registered position, the holes 24 and 32 are in register with one another, and the holes 22 are like aligned in register with one another.

The half-section 34 has a centerline B—B and the half-section 36 has a centerline C—C. The outer edge profile of the product condom article is shown in dashed outline by the dashed line S.

The blank in FIG. 1 may be die cut, laser cut, or cut and shaped in any suitable manner to provide the illustrated shape.

Figure 2:
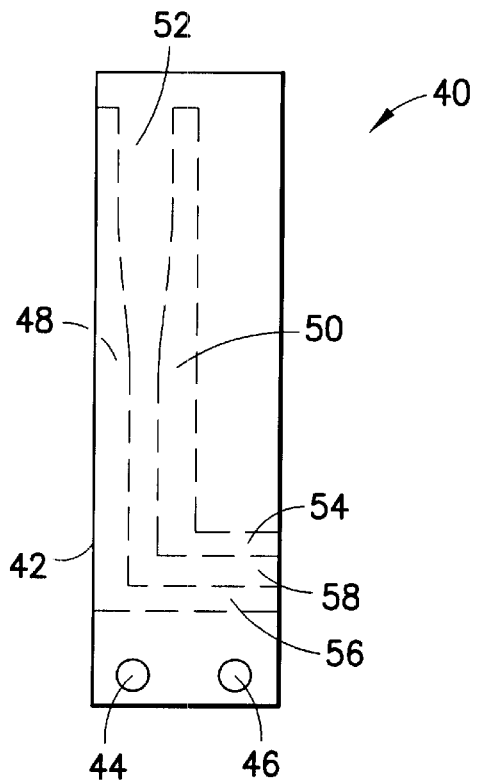
FIG. 2 is a valvular layer for forming an anti-reflux inflation valve for the inflatable condom article.

FIG. 2 is a valvular layer 40 for forming an anti-reflux inflation valve for the inflatable condom article. The valvular layer comprises a polymeric film sheet 42 which may be of a same or different material in relation to the sheet 12, but preferably is of a same material of construction.

The valvular layer sheet 42 at its lower edge region has two registration holes 44 and 46 therein for alignment with holes 26 and 28 in sheet 12 (see FIG. 1) when the respective layers are superposed as described hereinafter.

Outlined in dashed line representation on the valvular layer sheet 42 is an inlet structure whose arrangement and operation will be more fully apparent from the ensuing description. The inlet structure comprises portions within the dashed lines that are heat sealed in the subsequent assembly of the inflatable article. The inlet structure includes laterally spaced-apart longitudinally extending inlet walls 48 and 50 defining an inlet passage 52 therebetween, as well as the laterally extending legs 54 and 56 defining therebetween the transition passage 58.

Figure 3:
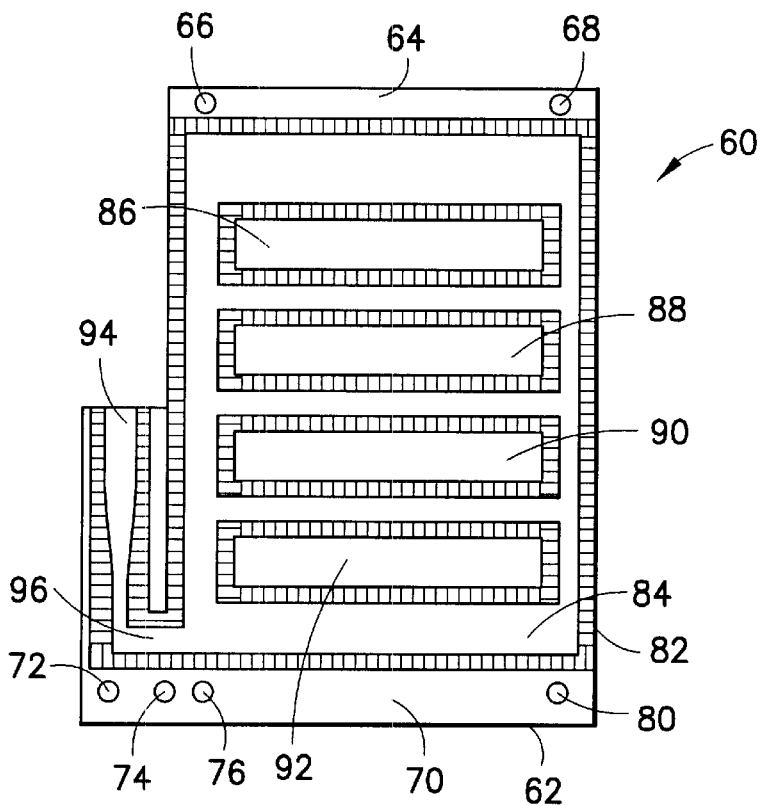
FIG. 3 is an inflation manifold layer for the inflatable condom article.

FIG. 3 is an inflation manifold layer 60 for the inflatable condom article. The inflation manifold layer 60 comprises a polymeric film sheet 62 that may be of a same or different material in respect of the sheet 12. The inflation manifold layer 60 has an upper edge 64 containing registration openings 66 and 68, and lower edge 70 having registration openings 72, 74 and 76 on the left-hand side thereof as illustrated and the single registration opening 80 on the right-hand side thereof.

The inflation manifold layer 60 is shown with cross-hatched heat-seal weld lines 82 demarcating an enclosed inflation compartment 84 bounded by the weld lines. The weld lines includes discrete rectangular welds bounding openings 86, 88, 90 and 92, and the inlet weld lines demarcating inlet passage 94 and transition passage 96 communicating with the inflation compartment 84.

Figure 4:
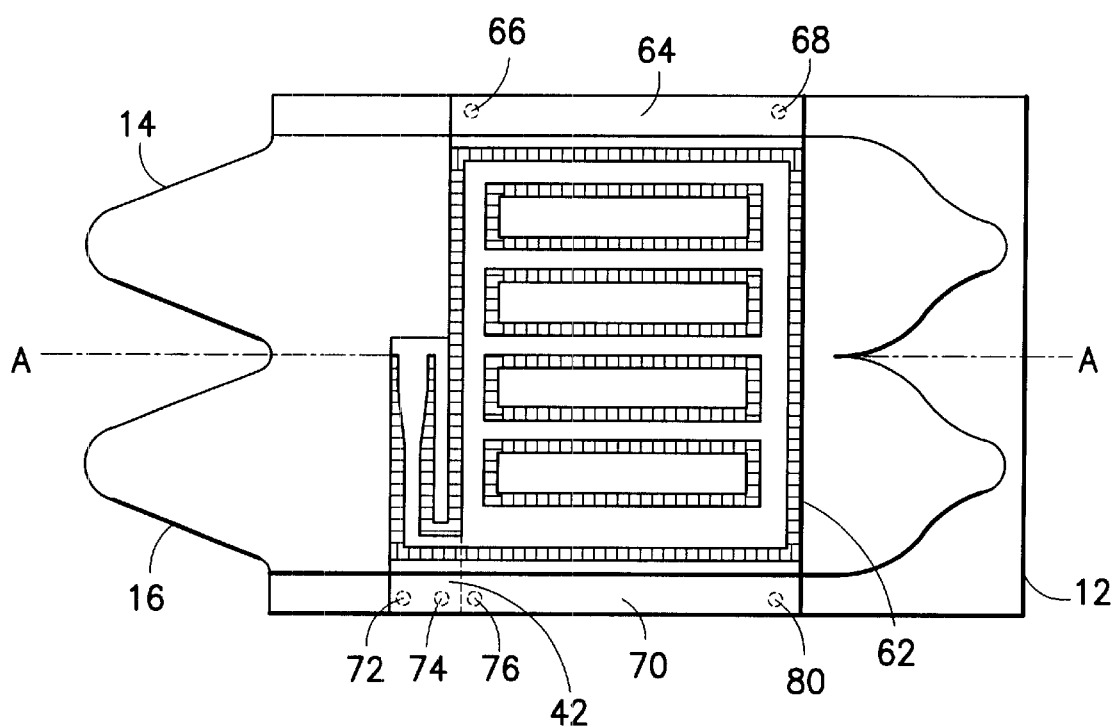
FIG. 4 is a superposed layer assembly after heat-sealing to form an intermediate article structure.

FIG. 4 is a superposed layer assembly after heat-sealing to form an intermediate article structure. To form the intermediate article structure illustrated, the blank 10 is secured on pins (pins not shown in FIG. 4) so that upstanding pins engage openings 22, 24, 26, 28, 20 and 32, to fixedly position the sheet 12.

Then two valvular layers 40 are sequentially overlaid on the sheet 12. A first valvular layer sheet 42 is positioned on sheet 12, with its registration holes 44 and 46 in registration with holes 26 and 28, so that hole 44 is over hole 26 on the same registration pin, and so that hole 46 is over hole 28 on another registration pin. Next, a second valvular layer 40 is overlaid on the first valvular layer sheet 42, with the second valvular layer sheet having its registration holes 44 and 46 in alignment with the registration holes 44 and 46 of the first valvular layer sheet.

With the two valvular layer sheets on the sheet 12 of the blank 10, the inflation manifold layer 60 is overlaid as shown in FIG. 4. In this arrangement, hole 72 of the inflation manifold layer sheet 62 overlies holes 44 of the double-thick valvular layer sheets and hole 26 of the sheet 12, while hole 74 of the inflation manifold layer sheet 62 overlies holes 46 of the double-thick valvular layer sheets and hole 28 of the sheet 12, as a 4-layer thickness of constituent layers at such region of the structure.

At the same time, holes 66, 68, 76 and 80 of the inflation manifold layer 60 are in registration with holes 22, 24, 30 and 32 of the polymeric film sheet 12, on respective registration pins, so that the superposed inflation manifold layer 60 and the polymeric film sheet 12 of the blank 10 form a two-layer thickness at such overlapped regions of the structure.

With the four constituent layers thus arranged as shown in FIG. 4, the assembly is heat-sealed along the weld lines previously described. The inlet structure thereby is a 4-ply structure and the main body portion of the inflation manifold layer is heat-sealed to the sheet 12 to form the enclosed inflation compartment 84 communicating via the transition passage 96 with the inlet passage 94.

The structure shown in FIG. 4 is then folded about the longitudinal centerline A—A so that the holes 66 and 68 are in register with the holes 76 and 80, respectively, on respective registration pins, and the peripheral edges of the superposed half-sections 34 and 36 are then welded along the dashed outline S (see FIG. 1), to form an enclosed tubular body. The welded body may be trimmed outside of the weld lines to remove excess material, relative to the final product shape desired.

Next, the valve area at the inlet is sealed, with the first and second layers being sealed to one another at the inlet, and the third and fourth layers being sealed to one another at the inlet, so as to form an inlet passage 94 of the desired character between the second and third layers.

Figure 5:
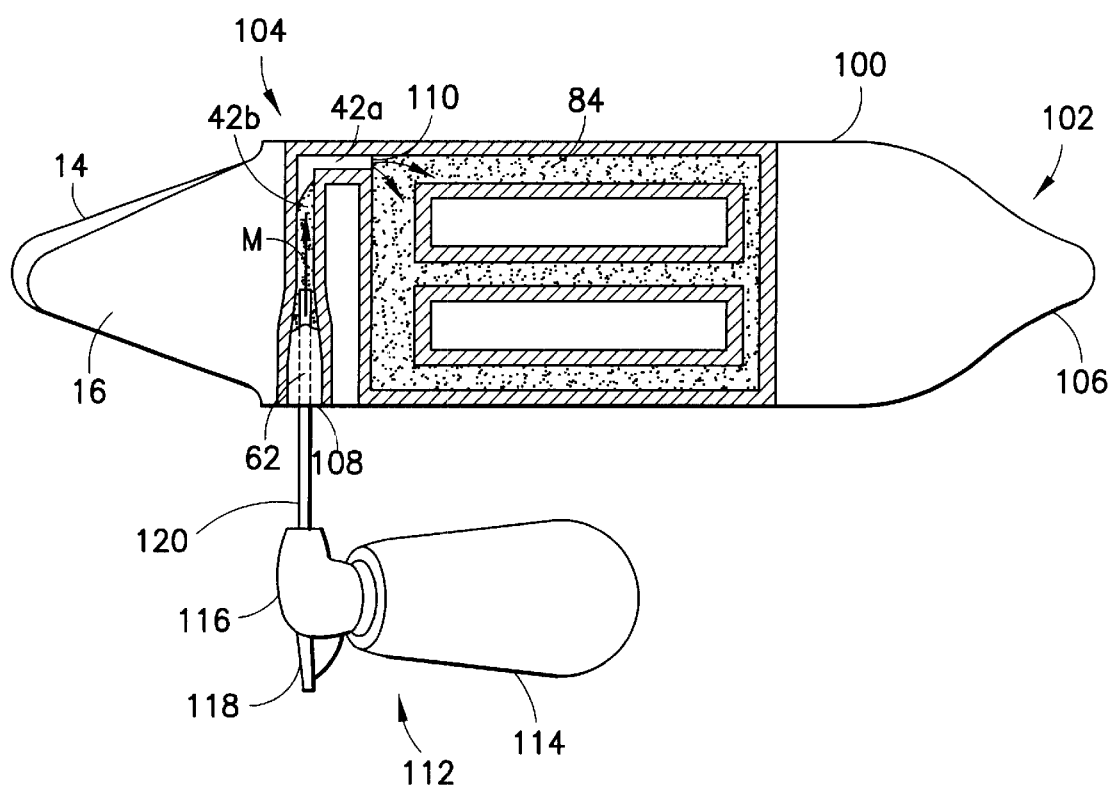
FIG. 5 is a perspective view of the fabricated inflatable condom article, shown with a compressed gas inflation accessory coupled to the condom in inflating relationship therewith.

FIG. 5 is a perspective view of the resulting fabricated inflatable condom article, shown with a compressed gas inflation accessory 112 coupled to the condom in inflating relationship therewith.

The condom article as shown has the sheet 62 overlying and bonded to the top valvular layer sheet 42*a* at the inlet. The bottom valvular layer sheet 42*b* overlies and is bonded to the sheet 12. In this manner, there is formed the inlet passage 94 between the valvular layer sheets 42*a* and 42*b* as shown in the partially broken away view of FIG. 5. The gas feed tube 120 is shown inserted into the passage 94, and discharging gas into the passage in the direction indicated by arrow M. The introduced gas flows through the inlet passage 94 and exits at the outlet end 110 of the transition passage, flowing thereafter into the enclosed inflation compartment 84 to fill same.

The gas feed tube 120 is fed from compressed gas reservoir 114 of the compressed gas inflation accessory 112. The compressed gas reservoir 114 is secured to a valve head 116 including a manually depressible spring-biased trigger for actuating the flow of gas from the reservoir into the gas feed tube 120. After inflation of the compartment, the gas feed tube is removed from the passage. The passage then is self-sealing, as a result of closure of the layers 42*a* and 42*b* against one another by virtue of the interior pressure in the compartment.

Specifically, when the inflation compartment of the condom is filled with gas, and the gas feed tube is removed, the back-pressure exerted by the gas in the compartment on the tube layers 42*a* and 42*b* of the assembly acts to force such layers 42*a* and 42*b* against each other, thereby closing the compartment so that it maintains its inflation.

The condom article 100 as shown has a distal end 102 that may include a tip reservoir 106 of known conformation, and a proximal end 104 having the rearwardly-extending proximal gripping flanges 14 and 16 associated therewith.

When the fill gas is dispensed into the enclosed inflation compartment 84, the condom structure is stiffened and rigidified by the fill gas. The fill gas may be introduced into the enclosed inflation compartment after the condom is donned, with the proximal gripping flanges 14, 16 facilitating the installation of the condom on the user's penis.

The gas-filled inflation compartment then functions to exert a compressive force on the penis at the base thereof, as well as along the length of the penis that is contiguous to the portion of the condom comprising the gas-filled inflation compartment. The rigidification that is imparted to the condom by the inflated compartment, together with the compressive force on the penis, thereby assists in maintaining the erection of the wearer.

It will be appreciated that the condom shown in FIG. 5 may be filled in any suitable manner other than by use of the accessory 112 that is shown in the drawing.

For example, the fill of the inflation compartment with gas may be effected by a tube of sufficient length to permit the user to blow into the tube to inflate the compartment, followed by removal of the tube in the same manner as described for the specific embodiment of FIG. 5.

As another alternative, a squeeze bulb or syringe or pump may be employed to introduce air or other gas into the inflation compartment.

Further, it will be appreciated that the inflation compartment in the specific condom embodiment illustrated may be widely varied in shape and/or areal extent on the condom.

For example, the inflation compartment may be coextensive with the entire length of the condom and the penis sheathed therein.

Alternatively, the inflation compartment may take the form of an inflation ring compartment at the proximal end of the condom to exert selective compressive circumferential force on the base of the penis for enhancement and maintenance of erection.

Still further, such a proximal end inflation ring compartment may have appended and concurrently inflatable extension segments for the purpose of providing clitoral stimulation to a female coital partner of the wearer of the condom.

Further, it will be appreciated that while the invention has been illustratively described in terms of a condom including an inflation compartment for enhancement and maintenance of the wearer's erection, and for prolongation of intercourse as a result of the rigidification of the condom, there are numerous other embodiments and applications in which the inflatable structure and anti-reflux valve of the invention can advantageously be employed.

Examples of such alternative applications of the invention include neck rest cushions, back rests, inflatable furniture, life preservers, balloons, packing materials, insulative compartments for garments, mattresses, pillows, toys, protective covers for vehicles (e.g., anti-hail damage covers that can be inflated on an automobile to protect it against hailstone impact), freeze protection covers for trees and shrubbery, and various other applications, e.g., where a selectively inflatable structure is desired for barrier formation, insulation, comfort, recreation, etc.

Although the invention has been variously disclosed herein with reference to illustrative aspects, embodiments and features, it will be appreciated that the aspects, embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. An inflatable structure comprising:

a sheath body;

an inflation compartment attached thereto, wherein said inflation compartment defines an enclosed interior volume; and an anti-reflux valve having an outlet end positioned in the interior volume, said anti-reflux valve comprising an elongate inflation passage including oppposedly facing film layers that are bonded to one another at their edges to form an interior gas flow channel, wherein said elongate inflation passage of said anti-reflux valve is bonded to the inflatable compartment to form an opening for introduction of gas into the passage, and arranged so that introduced gas flows through the interior gas flow channel, for discharge from the passage into the interior volume of the inflation compartment, with the elongate passage extending into the interior volume of the inflatable compartment to a sufficient extent so that upon termination of gas flow into the interior volume, after pressure in the interior volume has been raised above exterior pressure on the inflatable compartment, gas pressure in said interior volume will collapse the oppposedly facing film layers against one another to form a seal against the interior volume gas pressure and maintain the inflation compartment in an inflated state, and wherein said inflation compartment and said elongate inflation passage of the anti-reflux valve extend circumferentially over at least a portion of said sheath body and are attached thereon to form a unitary laminated structure therewith.

2. The inflatable structure of claim 1, wherein the oppposedly facing film layers of the elongate inflation passage at their outer edges are heat sealed to layers forming the inflation compartment and the sheath body to form said unitary laminated structure.

3. The inflatable structure of claim 1, wherein the inflation compartment and anti-reflux valve a re formed of a same film material.

4. The inflatable structure of claim 1, wherein at least one of said film layers and inflation compartment comprise a material having a modulus of elasticity at 50% elongation of from about 50 to about 1500 psi.

5. The inflatable structure of claim 1, wherein the inflation compartment is formed of a film material having a durometer value of from about 10 A to about 98 A.

6. The inflatable structure of claim 1, comprising a film material selected from the group consisting of: polyurethane; styrene-isoprene-styrene/styrene-butadiene-styrene compositions; plasticized polyvinylchloride; urethane/PVC blends; plasticized urethane; polyester elastomers; polyamide elastomers; olefinic polymers; and metallocene polymers.

7. The inflatable structure of claim 1, comprising a polyurethane film having a durometer not exceeding about 90 A.

8. The inflatable structure of claim 1, comprising a blown film.

9. The inflatable structure of claim 1, comprising an extruded sheet.

10. The inflatable structure of claim 1, comprising a solvent cast film.

11. The inflatable structure of claim 1, comprising a film having a thickness in the range of from about 1 to about 25 mils.

12. The inflatable structure of claim 1, comprising a film having a thickness in the range of from about 1 to about 10 mils.

13. The inflatable structure of claim 1, comprising a film having a thickness in the range of from about 2 to about 6 mils.

14. A condom article comprising an inflatable structure as in claim 1.

15. The condom article of claim 14, wherein the inflation compartment extends longitudinally and circumferentially over a portion of said sheath body and is heat-sealed thereto.

16. The condom article of claim 14, wherein the inflation compartment is arranged to exert circumferential pressure at the base of the penis of a wearer of the condom.

17. The condom article of claim 14, constructed and arranged as a male condom.

18. The condom article of claim 14, constructed and arranged as a female condom.

19. The condom article of claim 14, wherein the elongate inflation passage of said anti-reflux valve extends transversely and circumferentially over a portion of said sheath body and is heat sealed to layers forming the inflation compartment and the sheath body at its outer edges.

* * * * *